United States Patent
MacAllister et al.

(10) Patent No.: US 11,865,119 B2
(45) Date of Patent: Jan. 9, 2024

(54) METHODS OF TREATING AGITATION AND OTHER DEMENTIA-ASSOCIATED BEHAVIORAL SYMPTOMS

(71) Applicant: Woolsey Pharmaceuticals, Inc., St. Petersburg, FL (US)

(72) Inventors: Thomas MacAllister, Arlington, VA (US); Sven Jacobson, New York, NY (US)

(73) Assignee: WOOLSEY PHARMACEUTICALS, INC., St. Petersburg, FL (US)

( * ) Notice: Subject to any disclaimer, the term of this patent is extended or adjusted under 35 U.S.C. 154(b) by 0 days.

(21) Appl. No.: 18/177,188

(22) Filed: Mar. 2, 2023

(65) Prior Publication Data
US 2023/0201219 A1    Jun. 29, 2023

Related U.S. Application Data

(63) Continuation of application No. PCT/US2022/079861, filed on Nov. 15, 2022.

(60) Provisional application No. 63/283,696, filed on Nov. 29, 2021.

(51) Int. Cl.
*A61K 31/5513* (2006.01)
*A61P 25/28* (2006.01)
*A61K 9/00* (2006.01)

(52) U.S. Cl.
CPC .......... *A61K 31/5513* (2013.01); *A61P 25/28* (2018.01); *A61K 9/0053* (2013.01)

(58) Field of Classification Search
CPC ............................ A61K 31/5513; A61P 25/28
See application file for complete search history.

(56) References Cited

U.S. PATENT DOCUMENTS

| | | | |
|---|---|---|---|
| 9,980,972 | B2 | 5/2018 | Lingor et al. |
| 11,311,553 | B1 | 4/2022 | MacAllister et al. |
| 11,478,482 | B2 | 10/2022 | Ozaki et al. |
| 2005/0065170 | A1 | 3/2005 | Berg et al. |
| 2016/0272587 | A1 | 9/2016 | Wang et al. |
| 2019/0015404 | A1 | 1/2019 | Ruschel et al. |
| 2021/0213030 | A1 | 7/2021 | MacAllister et al. |
| 2021/0299140 | A1 | 9/2021 | MacAllister et al. |
| 2022/0047607 | A1 | 2/2022 | MacAllister et al. |
| 2022/0331333 | A1 | 10/2022 | Herault et al. |

FOREIGN PATENT DOCUMENTS

| | | |
|---|---|---|
| WO | 2008/019395 A2 | 2/2008 |
| WO | 2008/021210 A2 | 2/2008 |
| WO | 2009/155777 A1 | 12/2009 |
| WO | 2021/194607 A1 | 9/2021 |
| WO | 2021/216139 A1 | 10/2021 |
| WO | 2021/257122 A1 | 12/2021 |
| WO | 2022/015365 A1 | 1/2022 |
| WO | 2022/245708 A1 | 11/2022 |
| WO | 2022/245719 A1 | 11/2022 |

OTHER PUBLICATIONS

Palm, "Severe Agitation in Dementia: An Explorative Secondary Data Analysis on the Prevalence and Associated Factors in Nursing Home Residents", Journal of Alzheimer's Disease 66 (2018) 1463-1470.*
International Search Report of International Patent Application No. PCT/US22/79861, dated Feb. 7, 2023.
Kamei et al., "Evaluation of Fasudil Hydrochloride Treatment for Wandering Symptoms in Cerebrovascular Dementia with 31 P-Magnetic Resonance Spectroscopy and Xe-Computed Tomography", Clinical Neuropharmacology, 1996, pp. 428-438, vol. 19, No. 5.
Maust et al., "Antipsychotics, Other Psychotropics, and the Risk of Death in Patients With Dementia: Number Needed to Harm", JAMA Psychiatry, May 1, 2015, pp. 438-445, vol. 72, No. 5.
Greathouse et al., "Fasudil or genetic depletion of ROCK1 or ROCK2 induces anxiety-like behaviors", Behavioural Brain Research, 2019, pp. 1-4, vol. 373, Article No. 112083.
De Medeiros et al., "The Neuropsychiatric Inventory-Clinician rating scale (NPI-C): reliability and validity of a revised assessment of neuropsychiatric symptoms in dementia", Sep. 2010, Int Psychogeriatr., pp. 984-994, vol. 22, No. 6.
Kamei et al., "Effect of fasudil hydrochloride on wandering symptoms of cerebrovascular dementia patients", Neurotherapy, 1996, pp. 43-50, vol. 13, No. 1.
Yan et al., " Curative effect of Fasudil injection combined with Nimodipine on Alzheimer disease of elderly patients", Journal of Clinical Medicine in Practice, 2011, pp. 92-94-98, vol. 15, No. 13.
Lingor et al., "ROCK-ALS: Protocol for a Randomized, Placebo-Controlled, Double-Blind Phase IIa Trial of Safety, Tolerability and Efficacy of the Rho Kinase (ROCK) Inhibitor Fasudil in Amyotrophic Lateral Sclerosis", Clinical Study Protocol, Frontiers in Neurology, Mar. 27, 2019, pp. 1-11, vol. 10, Article 293.
Koch et al., "Compassionate Use of the ROCK Inhibitor Fasudil in Three Patients With Amyotrophic Lateral Sclerosis", Case Report, Frontiers in Neurology, Mar. 13, 2020, pp. 1-8, vol. 11, Article 173.
Lingor et al., "ROCK-ALS: a phase IIa clinical trial evaluating inhibition of Rho kinase (ROCK) with Fasudil as disease-modifying treatment for ALS", Universitatsmedizin Goettigen, poster, rock-als.uni-goettingen.de.
Huetelman et al., "Peripheral Delivery of a ROCK Inhibitor Improves Learning and Working Memory", Feb. 2009, pp. 218-223, vol. 123, No. 1.

(Continued)

*Primary Examiner* — Sahar Javanmard
(74) *Attorney, Agent, or Firm* — MCBEE MOORE & VANIK IP, LLC

(57) ABSTRACT

The invention is based on the discovery that rho kinase inhibitors, particularly fasudil can be used to treat agitation/anxiety in dementia patients, particularly Alzheimer's disease patients. Fasudil treatment of Alzheimer's patients resulted in improvements in agitation that are orders of magnitude to that observed with other potential therapeutic agents.

27 Claims, 3 Drawing Sheets

(56) References Cited

OTHER PUBLICATIONS

Tractenberg et al., "Comorbidity of Psychopathological Domains in Community-Dwelling Persons With Alzheimer's Disease", J. Geriatr. Psychiatry. Neurol., Jun. 2003, pp. 94-99, vol. 16, No. 2.

Ryu et al., "Persistence of and changes in neuropsychiatric symptoms in Alzheimer disease over 6 months: the LASER-AD study", Am. J. Geriatr. Psychiatry, Nov. 2005, pp. 976-983, vol. 13, No. 11—Abstract attached.

Charernboon et al., "Prevalence of neuropsychiatric symptoms in Alzheimer's disease: a cross-sectional descriptive study in Thailand", J Med Assoc Thai, 2014, pp. 560-565, vol. 97—Abstract attached.

* cited by examiner

METHODS OF TREATING AGITATION AND OTHER DEMENTIA-ASSOCIATED BEHAVIORAL SYMPTOMS

CROSS-REFERENCE TO RELATED APPLICATION

This is a bypass continuation of United States Patent Application No. PCT/US22/79861, filed November 2022, which is an International Application under the Patent Cooperation Treaty, claiming priority to U.S. Provisional Patent Application No. 63/283,696, filed 29 November 2021, related Applications the contents of both of which are incorporated herein by reference in their entirety.

BACKGROUND OF THE INVENTION

Agitation is common in Alzheimer's Disease (AD) patients and other dementia patients. Agitation in such patients can manifest as verbal or physical agitation, irritability, anxious affect, disinhibited behavior such as aggression, behavioral responses to delusions and hallucinations, and disrupted sleep and/or eating. Agitation can be triggered by changes in routine, surroundings, or caregivers; discomfort (hunger, pain, sleepiness), fear, anxiety, fatigue, medication, or navigating a confusing world. Patients experience increased agitation with increasing dementia severity. Charernboon and Phanasathit observed high rates of agitation, aggression, aberrant motor behaviors, and sleep problems in patients with AD, and found that the frequency of symptoms increased with the severity of illness. (Charernboon and Phanasathit 2014).

Agitation and/or aggression are estimated to affect up to approximately 80% of patients with dementia (Ryu 2005; Tractenberg 2003). Agitation in AD and dementia patients leads to caregiver stress, increased morbidity and mortality for the patients, and earlier placement into care facilities. Agitation and irritability, in particular, pose a threat to the health and quality of life of dementia patients. For example, common paranoid delusions in agitated dementia patients include beliefs that the house has been invaded, that personal objects have been misplaced or stolen, that family members have been replaced by impostors, or that spouses have been unfaithful.

Current treatment of AD includes non-pharmacological and pharmacological approaches as necessary. Non-pharmacological, behavioral approaches are a challenge and take time to implement, which is not conducive for care facilities where poor staff to resident ratios exist. Other non-pharmacological approaches include aromatherapy, lighting intervention, and ambient music therapy. Many patients fail to respond to the non-pharmacological approaches and pharmacotherapy is often needed. There are currently no FDA-approved pharmacological treatments for agitation in Alzheimer's disease, and clinicians therefore resort to off-label use of antipsychotics, sedatives/hypnotics, anxiolytics, and antidepressants to attempt to control symptoms. Common medications used to treat agitation include beta blockers such as propranolol and pindolol, anxiety medications such as buspirone, anti-convulsants such as valproate and lamotrigine, anti-psychotics such as haloperidol and other high-potency dopamine-blocking agents and atypical antipsychotics. In AD, for example, pharmacological treatment frequently includes use of atypical antipsychotics which have modest effects that are outweighed by safety and efficacy concerns leading to "black box" warnings by the U.S. Food and Drug Administration (FDA). There is an increased risk of death and potentially life-threatening side effects when such antipsychotics are used, especially at higher doses. (Maust 2015). Other adverse effects of antipsychotic use include increased cerebrovascular events, gait abnormality, falls, and metabolic syndrome.

US Food and Drug Administration (FDA) recently approved pimavanserin for dementia-related psychosis in Parkinson's disease, and this drug is currently in clinical trials to treat both psychosis and agitation in patients with AD and in a trial for dementia-related psychosis in multiple types of neurodegenerative disorders. Pimavanserin is a selective 5-HT2A receptor inverse agonist.

There is an ongoing need for lower risk pharmacological agents to treat agitation and anxiety in AD and in other dementia patients, and in other disorders in which agitation and anxiety are symptoms.

SUMMARY OF THE INVENTION

In one embodiment, provided is a method for treating agitation in a patient in need thereof with an effective amount of fasudil.

In one embodiment, provided is a method of treating a patient with agitation-associated dementia, comprising treating said patient with a therapeutically effective amount of fasudil.

In some embodiments, the dementia results, for example, from Alzheimer's Disease (AD), Parkinson's Disease (PD), Huntington's Disease (HD), amyotrophic lateral sclerosis (ALS), Dementia with Lewy Bodies (DLB), Frontotemporal Dementia (FTD), cerebrovascular dementia, mixed dementia, dementia not otherwise specified, normal pressure hydrocephalus (NPH) and head injuries, among others.

In a preferred embodiment, the dementia is Alzheimer's Disease (AD), which is the most common cause of dementia, accounting for 60-80% of cases. (Alzheimer's Association. Alzheimers Dement 2016; 12(4):459-509).

A preferred aspect of the invention contemplates a method of treating a patient with agitation due to cortical dementia, comprising treating said patient with a therapeutically effective amount of fasudil. In certain aspects of this embodiment, the cortical dementia is a proteinopathy-associated dementia. Examples of cortical dementia are Alzheimer's (AD), Vascular Dementia, Lewy Body (LBD), Frontotemporal Dementia), Frontotemporal Lobar (FTD), and Primary Progressive Aphasia (PPA)).

In another embodiment, the patient treated for agitation has a subcortical dementia. Examples of subcortical dementia are Binswanger's disease (BD; lacunar dementia), Parkinson's Disease (PD), Huntington's Disease (HD) and Multiple Sclerosis (MS).

In another embodiment the patient treated with fasudil for agitation has agitation associated with attention-deficit hyperactive disorder, conduct disorder, oppositional defiant disorder, Tourette's Syndrome, Lesch-Nyhan Syndrome, or disinhibitory symptoms of post-traumatic stress disorder.

In a specific embodiment, the fasudil administered to the patient with agitation is fasudil hydrochloride hemihydrate.

In one embodiment, the fasudil is administered to the patient in a dose from about 90 to 240 mg/day as an immediate release formulation.

In another embodiment, the fasudil is administered to the patient in an extended-release formulation, wherein the maximum plasma concentration and area under the curve in plasma over 24 hours do not exceed by more than 15% what is obtained using a dosing regimen of 90 to 240 mg/day as an immediate release formulation.

In a specific embodiment, the fasudil is administered to the patient two times per day (BID) or three time per day (TID).

In another specific embodiment, the fasudil is administered to the patient in a dose of 90 mg TID.

In a certain preferred embodiment, the inventive methods include method of treating a patient with agitation due to dementia, comprising treating said patient with a therapeutically effective amount of fasudil, where said patient has not previously been treated with fasudil for chronic stroke.

In another embodiment, the dementia patient to be treated for agitation does not have or have a history of depression, anxiety, or schizophrenia.

In another embodiment, the dementia patient to be treated does not exhibit wandering behavior such as elopement, boundary transgressions, or wayfinding defects.

In a further embodiment, the dementia patient to be treated does not exhibit pacing, looping, or excess walking.

In certain preferred embodiments, treated patients have a measurable minimum amount of agitation before commencing treatment. As measured by the NPI-Q agitation/aggression domain, certain patients may have a minimum score of 4 and on the full NPI certain patients will typically have a minimum agitation/aggression domain score of 6. As assessed by the CMAI-C, certain patients will have a threshold baseline minimum score of at least 5 and generally at least or 15, with a preferred minimum of 20. Minimum scores of 16, 17, 18, 19, 21, 22, 23, 24 and are also contemplated.

In some embodiments, the improvement by treatment with fasudil in in agitation and/or aggression and/or associated symptoms in subjects with dementia, such as AD, may be measured by improvements of one or more of the Clinical Global Impressions-Severity (CGI-S) scale for agitation; the Cohen-Mansfield Agitation Inventory, clinician version (CMAI-C); the Behavioral Pathology in Alzheimer's Disease; and the Neuropsychiatric Inventory (NPI) including the agitation subscales.

In one embodiment, the improvement in agitation with fasudil is assessed using the CMAI. In an embodiment, an improvement with fasudil is at least 2.5 points, at least 5 points, at least 10 points, at least 12 points, at least 20 points, or at least 25 points.

In one embodiment, the improvement in agitation with fasudil treatment is assessed using the NPI-Q and or the NPI4D score. For the NPI-Q, a score of 0 is the absence of symptoms and a score of 12 reflects daily occurrence of symptoms with marked severity.

In another embodiment, the patient's NPI4A score is reduced by at least 2.5 compared to the patient's baseline score prior to fasudil administration.

In one embodiment, the patient's NP14A score is reduced by at least 3.0 compared to the patient's baseline score prior to fasudil administration In other embodiments, treatment with fasudil reduces the agitation in the patient by at least 10%; 15%; 20%; 25%; 30%; 35%; 40%; 45% or 50% compared to baseline, i.e., the amount of agitation prior to fasudil treatment.

In another embodiment, treatment with fasudil reduces the amount of agitation by 50% or more.

In a specific embodiment, fasudil treatment reduces the number of occurrences of agitation, such as from multiple occurrences daily to one or none per day, or from occurrences every day to less than every day.

In a further embodiment, treatment with fasudil reduces the number of days per week agitation occurs by at least one day per week, preferably by at least two days per week, and more preferably by at least three days per week.

In another embodiment, treatment with fasudil reduces the severity of the agitation, such by reducing the number of occurrences of verbal or physical aggression.

In another specific embodiment, fasudil treatment reduces the number of occurrences of "sundowning" per week or per month. In a further embodiment, fasudil treatment reduces the length of time or the progression of sundowning evening agitation. In a further embodiment, fasudil reduces the severity of the behavior associated with sundowning.

In another embodiment, treatment with fasudil reduces or halts the increased agitation that occurs with progression of dementia.

In another embodiment, treatment with fasudil reduces aberrant motor activity in dementia patients by at least 10%; 15%; 20%; 25%; 30%; 35%; 40%; 45% or 50%. In a specific embodiment, treatment with fasudil reduces the aberrant motor activity occurs during sundowning, or early evening.

In another embodiment, treatment with fasudil reduces sleep disturbances such as insomnia in dementia patients by at least 10%; 15%; 20%; 25%; 30%; 35%; 40%; 45% or 50%. In a specific embodiment, the number of incidences per week of insomnia is reduced.

In another embodiment, treatment with fasudil reduces the number of occurrence of delusions or hallucinations behavior by at least 10%; 15%; 20%; 25%; 30%; 35%; 40%; 45% or 50%.

In yet another embodiment, treatment with fasudil reduces anxiety in dementia patients by at least 10%; 15%; 20%; 25%; 30%; 35%; 40%; 45% or 50%.

In another embodiment, treatment with fasudil reduces disinhibition in dementia patients by at least 10%; 15%; 20%; 25%; 30%; 35%; 40%; 45% or 50%.

In a further embodiment, treatment with fasudil reduces hostility and suspiciousness in dementia patients by at least 10%; 15%; 20%; 25%; 30%; 35%; 40%; 45% or 50%.

In another embodiment, treatment with fasudil reduces eating or appetite disturbances in dementia patients by at least 10%; 15%; 20%; 25%; 30%; 35%; 40%; 45% or 50%.

In another embodiment, treatment with fasudil reduces the caregiver burden associated with agitation by at least 10%; 15%; 20%; 25%; 30%; 35%; 40%; 45% or 50%.

In one embodiment, the dementia patient with agitation is male.

DETAILED DESCRIPTION OF THE INVENTION

Figure 1:
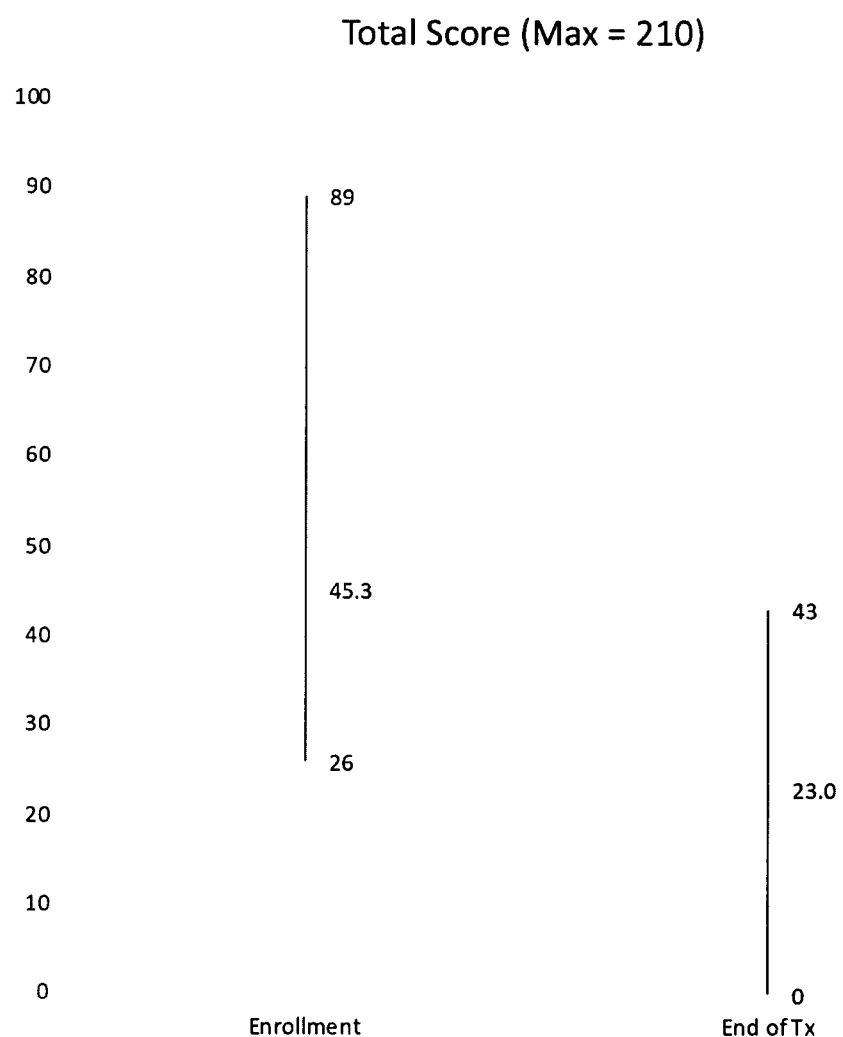
FIG. 1 shows the change from baseline in the mean CMAI score for six patients treated with fasudil who had an NPI-Q score of ≥4 prior to treatment.

The invention is based on the discovery that rho kinase inhibitors such as fasudil can be used to treat agitation associated with dementia. Fasudil, an inhibitor of rho kinase, has been reported to have a number of potentially beneficial effects in conditions of the CNS, although no there is no Level 1 evidence of treatment effect in any condition, meaning any potential medical application remains speculative.

Greathouse et al., Behavioural Brain Research. 2019; 373:112083, report that depletion of rho kinases or treatment with fasudil induces anxiety-like behavior in mice. Six-month old mice were dosed with 10 mg/kg fasudil or water by oral gavage once a day for 30 days. Behaviors were assessed over the final 3 days of drug treatment by elevated plus maze and open field. Fasudil treatment significantly reduced the amount of time the mice spent in the "open arms" part of the maze, indicating anxiety. Genetic reduction of rho kinase inhibitors (heterozygotes for ROCK1 and ROCK2) exhibited the same behavior. It is commonly understood that anxiety and agitation are strongly associated, and that agitation may be caused by anxiety. The present invention is based on the surprising discovery that, despite the anxiety-producing effects of fasudil in mice, it can be successfully employed in the treatment of agitation.

The term "agitation," as used in this disclosure, is includes the definition of agitation as described by Cummings et al., International Psychogeriatrics. 2015; 27(1):7-17. Broadly, Cummings et al. define agitation as: 1) occurring in patients with a cognitive impairment or dementia syndrome; 2) exhibiting behavior consistent with emotional distress (e.g. rapid changes in mood, anxiety, irritability, outbursts, etc.) and the behavior has been persistent or frequently recurrent for a minimum of two weeks and is a change from the patient's usual behavior; 3) the behaviors are severe enough to produce excess disability; and 4) and the agitation is not solely attributable to another disorder (psychiatric, suboptimal care conditions, medical, or substance-related).

Agitation also includes "sundowning," which refers to behavioral disturbances that peak in the late afternoon or evening. Sundowning affects up to two-thirds of patients with dementia and is closely related to disturbed circadian rhythms.

Several rating scales are used to assess agitation, including the Cohen-Mansfield Agitation Inventory (CMAI, Cohen-Mansfield 1986), the Behavioral Pathology in Alzheimer's Disease (BEHAVE-AD frequency rated scale; Monteiro 2001), and the widely used Neuropsychiatric Inventory (NPI; de Medeiros 2010). The Agitated Behavior Scale (ABS) was developed to assess the nature and extent of agitation during the acute phase of recovery from acquired brain injury.

The 29-item CMAI was designed to measure types and frequencies of agitated behavior. It is the most commonly used assessment, considered to be the current "gold standard" and the only outcome measure accepted to date by the regulatory authorities for approving pharmaceutical interventions for agitation. The CMAI consists of 29 items forming four subscales; physically aggressive behavior (e.g. hitting others), physically non-aggressive behavior (e.g. pacing), verbally aggressive (e.g. swearing) and verbally non-aggressive behaviors (e.g. repetitive sentences). The CMAI incorporates both the frequency and severity of behaviors associated with agitation and allows the quantification of agitated behaviors into a continuous measure, which is sensitive to change. The CMAI asks the assessor to rate the subject's behavior for the previous 2 weeks.

The CMAI-C is a 37-item scale to systematically assess agitation using 35 specific symptoms, the time of day of the behavior, and the frequency of "other" behaviors. Subjects are rated by regarding the frequency with which they manifest physically aggressive, physically non-aggressive and verbally agitated behaviors on a 7-point scale from never (0) to several times and hour (6). The CMAI-C also asks the assessor to rate the subject's behavior for the previous 2 weeks.

The NPI is an assessment that evaluates 12 behavioral areas and effects on treatment in dementia patients. The total NPI score is the composite of the scores for the standard 12 NPI domains: delusions, hallucinations, agitation/aggression, dysphoria/depression, anxiety, euphoria/elation, apathy/indifference, disinhibition, irritability/lability, aberrant motor behaviors, nighttime behavioral disturbances, and appetite/eating disturbances. The scripted NPI interview includes a compound screening question for each symptom domain, followed by a list of interrogatives about domain-specific behaviors that is administered when a positive response to a screening question is elicited. Each of the 12 items is scored based on the product of its frequency (1-4; occasionally, often, frequently and very frequently) by its severity (1-3; mild, moderate and marked) resulting in total scores up to 144. (Cummings 1997) Frequency and severity rating scales have defined anchor points to enhance the reliability of caregiver responses. Caregiver distress is rated for each positive neuropsychiatric symptom domain on a scale anchored by scores of 0 (not distressing at all) to 5 (extremely distressing).

The original NPI included 10 neuropsychiatric domains; two others, Nighttime Behavioral Disturbances and Appetite/Eating Changes, were subsequently added. Another recent modification of the original NPI is the addition of a Caregiver Distress Scale for evaluating the psychological impact of neuropsychiatric symptoms reported to be present (Kaufer 1998). The NPI-Q includes both these additions.

The NPI-C, the clinician-rated form of the NPI has a broader range that includes neuropsychiatric characteristics of MCI and severe dementia, high inter-rater reliability, strong convergent validity for depression (assessed with the Cornell Scale for Depression in Dementia [CSDD]), psychosis (assessed with the Brief Psychiatric Rating Scale [BPRS]), apathy (vs. Apathy Evaluation Scale [AES]), and agitation/aggression (vs. the CMAI).

One subdomain of the NPI is the NPI4A, which is the composite score comprising the NPI agitation/aggression, aberrant motor behavior, irritability/lability, and anxiety domains. (Dennehy 2013).

Other rating scales are also used. The Alzheimer's Disease Cooperative Study-Clinical Global Impression of Change (ADCS-CGIC, shortened to "CGIC") uses an interview structure with worksheets to remind raters to evaluate specific neuropsychiatric symptoms. The ADCS-CGIC evaluates the patient in five treatment domains: 1) cognition (immediate and delayed memory, praxis, attention, and executive function); 2) clinical global change; 3) activities of daily living; 4) behavioral symptoms (agitation and other noncognitive symptoms); 5) cognition in severely impaired patients. (Schneider 1997). The ADCS-CGIC focuses on clinicians' observations of change in the patient's cognitive, functional, and behavioral performance since the beginning of a trial. Unlike a targeted symptom scale, it takes into account a subject's overall function in the cognitive, behavioral and functional activity domains. Scoring is based on an interview with the caregiver and examination of the patient by an independent evaluator, without consulting other information such as cognitive test results. The ADCS-CGIC measures: global severity at baseline scored from 1 (normal, not at all ill) to 7 (among the most extremely ill patients);

and global change at follow-up scored from 1 (marked improvement) to 7 (marked worsening), where 4 indicates no change.

The BEHAVE-AD (caregiver version) and the empirical version (E-BEHAVE AD) is a reliable and valid clinician interview rated 12-item instrument developed to assess behavioral pathology in Alzheimer's disease and related dementia. It rates 12 symptoms as 0-3 (no present to severely present) resulting in a total score up to 36. The Neurobehavioral Rating Scale (NBRS) is a 27-item observer-rated scale that measures a broad range of cognitive and non-cognitive symptoms, including disinhibition, i.e., the ability to inhibit inappropriate behavior, and agitation. It has 6 levels ranging from "not present" to extremely severe. NBRS target symptoms include: aggression, agitation, hostility, delusions, hallucinations and suspiciousness.

ROCK Inhibitors

The inventive methods contemplate the administration of a rho kinase (ROCK) inhibitor fasudil in the treatment of a disease or condition. Two mammalian ROCK homologs are known, ROCK1 (aka ROKβ, Rho-kinase β, or p160ROCK) and ROCK2 (aka ROKα) (Nakagawa 1996). In humans, the genes for both ROCK1 and ROCK2 are located on chromosome 18. The two ROCK isoforms share 64% identity in their primary amino acid sequence, whereas the homology in the kinase domain is even higher (92%) (Jacobs 2006; Yamaguchi 2006). Both ROCK isoforms are serine/threonine kinases and have a similar structure.

The inventive methods contemplate the administration of a rho kinase (ROCK) inhibitor in the treatment of a disease or condition. Two mammalian ROCK homologs are known, ROCK1 (aka ROKβ, Rho-kinase β, or p160ROCK) and ROCK2 (aka ROKα) (Nakagawa 1996). In humans, the genes for both ROCK1 and ROCK2 are located on chromosome 18. The two ROCK isoforms share 64% identity in their primary amino acid sequence, whereas the homology in the kinase domain is even higher (92%) (Jacobs 2006; Yamaguchi 2006). Both ROCK isoforms are serine/threonine kinases and have a similar structure.

A number of pharmacological ROCK inhibitors are known (Feng, LoGrasso, Defert, & Li, 2015). Isoquinoline derivatives are a preferred class of ROCK inhibitors. The isoquinoline derivative fasudil was the first small molecule ROCK inhibitor developed by Asahi Chemical Industry (Tokyo, Japan). The characteristic chemical structure of fasudil consists of an isoquinoline ring, connected via a sulphonyl group to a homopiperazine ring. Fasudil is a potent inhibitor of both ROCK isoforms.

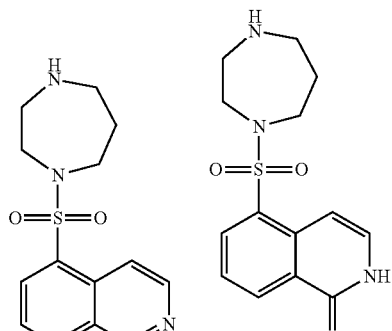

Fasudil    Hydroxyfasudil

In vivo, fasudil is subjected to hepatic metabolism to its active metabolite hydroxyfasudil (aka, M3). Other examples of isoquinoline derived ROCK inhibitors include dimethylfasudil and ripasudil.

Other preferred ROCK inhibitors are based on based on 4-aminopyridine structures. These were first developed by Yoshitomi Pharm. (Uehata et al., 1997) and are exemplified by Y-27632. Still other preferred ROCK inhibitors include indazole, pyrimidine, pyrrolopyridine, pyrazole, benzimidazole, benzothiazole, benzothiophene, benzamide, aminofurazane, quinazoline, and boron derivatives (Feng et al., 2015). Exemplary ROCK inhibitors are shown below:

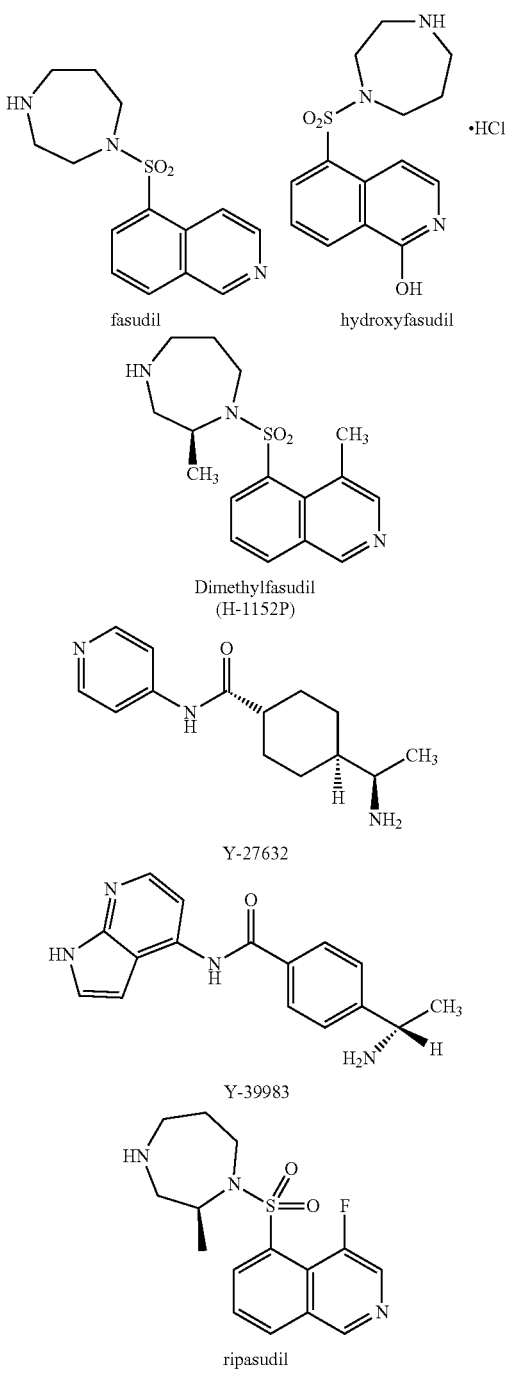

ROCK inhibitors according to the invention may have more selective activity for either ROCK1 or ROCK2 and will usually have varying levels of activity on PKA, PKG, PKC, and MLCK. Some ROCK inhibitors may be highly specific for ROCK1 or ROCK2 and have much lower activity against PKA, PKG, PKC, and MLCK.

Fasudil is a preferred ROCK inhibitor to treat agitation according to the invention. The isoquinoline derivative fasudil was the first small molecule ROCK inhibitor developed by Asahi Chemical Industry (Tokyo, Japan). The characteristic chemical structure of fasudil consists of an isoquinoline ring, connected via a sulphonyl group to a homopiperazine ring. Fasudil is a potent inhibitor of both ROCK isoforms. In vivo, fasudil is subjected to hepatic metabolism to its active metabolite hydroxyfasudil (aka, M3). Other examples of isoquinoline derived ROCK inhibitors include dimethylfasudil and ripasudil.

Fasudil may exist as a free base or salt and may be in the form of a hydrate, such as a hemihydrate. As used herein, it will be understood that methods specifying the active moiety of a ROCK inhibitor apply equally to the free acids or free bases, salts, hydrates, polymorphs and prodrug derivatives thereof.

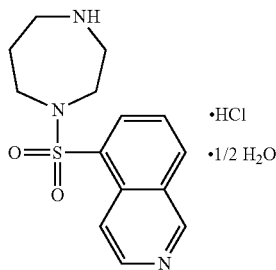 [SMILES: O=S(=O)(c1cccc2cnccc12)N1CCCNCC1 ; Cl]

Hexahydro-1-(5-isoquinolinesulfonyl)-1H-1,4-diazepine monohydrochloride hemihydrate Fasudil is a selective inhibitor of protein kinases, such as ROCK, PKC and MLCK and treatment results in a potent relaxation of vascular smooth muscle, resulting in enhanced blood flow (Shibuya 2001). A particularly important mediator of vasospasm, ROCK induces vasoconstriction by phosphorylating the myosin-binding subunit of myosin light chain (MLC) phosphatase, thus decreasing MLC phosphatase activity and enhancing vascular smooth muscle contraction. Moreover, there is evidence that fasudil increases endothelial nitric oxide synthase (eNOS) expression by stabilizing eNOS mRNA, which contributes to an increase in the level of the potent vasodilator nitric oxide (NO), thereby enhancing vasodilation (Chen 2013).

Fasudil has a short half-life of about 25 minutes, but it is substantially converted in vivo to its 1-hydroxy (M3) metabolite. M3 has similar effects to its fasudil parent molecule, with slightly enhanced activity and a half-life of about 8 hours (Shibuya 2001). Thus, M3 is likely responsible for the bulk of the in vivo pharmacological activity of the molecule.

Included in the invention are pharmaceutically acceptable salts and hydrates of fasudil. Salts that may be formed via reaction with inorganic and organic acid. Those inorganic and organic acids are included as following: hydrochloric acid, hydrobromide acid, hydriodic acid, sulfuric acid, nitric acid, phosphoric acid, acetic acid, maleic acid, maleic acid, maleic acid, oxalic acid, oxalic acid, tartaric acid, malic acid, mandelic acid, trifluoroacetic acid, pantothenic acid, methane sulfonic acid, or para-toluenesulfonic acid.

Methods of Treatment

The present invention contemplates treating agitation in dementia patients, especially AD patients. In one embodiment, fasudil is administered to dementia patients exhibiting agitation.

In a specific embodiment, the CMAI-C score at baseline for aggressive behavior, non-aggressive agitated behavior, and verbally agitated behavior is between about 13 and 15.

In another specific embodiment, the patient has a minimum NPI-Q agitation/aggression domain score of ≥4 or an NPI agitation/aggression domain score of ≥6 prior to administering the first dose of fasudil.

In some embodiments, reductions in agitation are assessed using one or more of the following: NPI-Q, CMAI-C, ADCS-CGIC, BEHAVE-AD, ABS, and NBRS, or agitation/aggression subscales thereof as applicable.

In a specific embodiment of the invention, the fasudil-treated patient's CMAI-C score for agitation/aggression is reduced by at least 5 points from baseline in dementia patients treated with fasudil. In other embodiments, CMAI-C score for agitation/aggression is reduced by at least 10 points, at least 12 points, at least 15 points, at least 20 points or at least 25 points from baseline following treatment with fasudil. It is specifically contemplated that improvements on the CMAI-C may be driven by one or more domains of the CMAI-C, including the verbally aggressive, verbally non-aggressive, physically aggressive, physically non-non-aggressive domains.

In another embodiment, the fasudil-treated patient's CGIC score of agitation is improved by at least 0.5 in patients treated with fasudil compared to untreated subjects or subjects administered a placebo.

In another embodiment, the patient's NPI4A score is reduced by at least 2.5 compared to the patient's baseline score prior to fasudil administration.

In one embodiment, the patient's NP14A score is reduced by at least 3.0 compared to the patient's baseline score prior to fasudil administration.

In one specific embodiment, treatment with fasudil reduces the agitation in patients by at least 10%; 15%; 20%; 25%; 30%; 35%; 40%; 45% or 50% compared to baseline, i.e., the amount of agitation prior to fasudil treatment.

In another embodiment, treatment with fasudil reduces the amount of agitation by 50% or more.

In a specific embodiment, fasudil treatment reduces the number of occurrences of agitation, such as from multiple occurrences daily to one or none per day, or from occurrences every day to less than every day.

In a further embodiment, treatment with fasudil reduces the number of days per week agitation occurs by at least one day per week, preferably by at least two days per week, and more preferably by at least three days per week.

In another embodiment, treatment with fasudil reduces the severity of the agitation, such by reducing the number of occurrences of verbal or physical aggression.

In another specific embodiment, fasudil treatment reduces the number of occurrences of "sundowning" per week or per month. In a further embodiment, fasudil treatment reduces the length of time or the progression of sundowning evening agitation. In a further embodiment, fasudil reduces the severity of the behavior associated with sundowning.

In another embodiment, treatment with fasudil reduces aberrant motor activity in dementia patients by at least 10%; 15%; 20%; 25%; 30%; 35%; 40%; 45% or 50%. In another embodiment, treatment with fasudil reduces sporadic wandering by 50% or more. In another embodiment, treatment with fasudil reduces the aberrant motor activity occurs during sundowning, or early evening. In one embodiment, the reduction of aberrant motor activity can be measured using electronic motion and/or activity tracking device, including fitness trackers such as Fitbits. The fitness trackers can be used alone or in combination with GPS devices to measure location.

In another embodiment, treatment with fasudil reduces sleep disturbances such as insomnia in dementia patients by at least 10%; 15%; 20%; 25%; 30%; 35%; 40%; 45% or 50%. In a specific embodiment, the number of incidences per week of insomnia is reduced.

In another embodiment, treatment with fasudil reduces the number of occurrence of delusions or hallucinations behavior by at least 10%; 15%; 20%; 25%; 30%; 35%; 40%; 45% or 50%.

In yet another embodiment, treatment with fasudil reduces anxiety in dementia patients by at least 10%; 15%; 20%; 25%; 30%; 35%; 40%; 45% or 50%.

In another embodiment, treatment with fasudil reduces disinhibition in dementia patients by at least 10%; 15%; 20%; 25%; 30%; 35%; 40%; 45% or 50%.

In a further embodiment, treatment with fasudil reduces hostility and suspiciousness in dementia patients by at least 10%; 15%; 20%; 25%; 30%; 35%; 40%; 45% or 50%.

In another embodiment, treatment with fasudil reduces eating or appetite disturbances in dementia patients by at least 10%; 15%; 20%; 25%; 30%; 35%; 40%; 45% or 50%.

In another embodiment, treatment with fasudil reduces the caregiver burden associated with agitation by at least 10%; 15%; 20%; 25%; 30%; 35%; 40%; 45% or 50%.

In one embodiment, the dementia patient with agitation is male.

Dosage and Administration

In accordance with the treatment methods of the present invention, an effective amount of fasudil or a pharmaceutically acceptable salt thereof such as fasudil hydrochloride hemihydrate for administration one or more times a day may comprise from about 10 mg to about 1000 mg. Fasudil hydrochloride hemihydrate, for example, is suitably administered in a daily amount of about 10 mg to about 500 mg, about 10 mg to about 400 mg, about 10 mg to about 200 mg, about 10 mg to about 100 mg, about 20 mg to about 10 mg.

One preferred dosing regimen involves the treatment with 25, 30 or 40 mg of fasudil hydrochloride hemihydrate three times per day using an immediate-release formulation, for a total daily dose of 75-120 mg. Most preferred dosing exceeds a daily dose of 70 mg, with most preferred ranges for daily dosing being 90 to 180 mg administered in three equal amounts during the day.

A particularly preferred daily dose is 90 mg/day administered 30 mg TID immediate release tablets. Fasudil is most preferably administered orally in accordance with the foregoing using an immediate release formulation. In another embodiment, fasudil is administered in a dose of 180 mg/day administered 60 mg TID immediate-release tablets.

Another embodiment involves the treatment with 90-180 mg of fasudil hydrochloride hemihydrate once per day in an extended-release dosage form. Treatment with an extended-release total daily dose of 90 mg fasudil hydrochloride hemihydrate once per day is preferred.

In one embodiment, the fasudil is administered to the patient in a dose from about 90 to 240 mg/day as an immediate release formulation.

In another embodiment, the fasudil is administered to the patient in an extended-release formulation, wherein the maximum plasma concentration and area under the curve in plasma over 24 hours do not exceed by more than 15% what is obtained using a dosing regimen of 90 to 240 mg/day as an immediate release formulation.

It will be appreciated that dose ranges as described herein provide guidance for the administration. Certain patient sub-populations, such as renally impaired patients and/or older patients (e.g., 65 or older) may need lower doses or extended-release formulations instead of immediate release formulations. Fasudil hydrochloride hemihydrate may have higher steady-state concentrations when given at usual doses to patients with renal disease and lower doses to lower the Cmax or delay the time to Cmax (increase the Tmax) may be required.

In addition, older patients, typically those with dementia, may need a lower dose at initiation, with a gradual increase to the recommended dose after days or weeks. In another embodiment, older patients may need lower doses for the duration of treatment. The aged population includes the "young old" who are 65-74, the "old old" who are 75-84 and the "frail elderly" who are 85 and older. For example, a starting dose of 30 mg per day for two weeks, followed by 60 mg per day for 4 weeks, then by 90 mg per day. Titration may even be warranted up to about 180 mg per day.

Methods of administering compositions according to the invention would generally be continued for at least one day. Some preferred methods treat for up to 30 days or up to 60 days or even up to 90 days or even more. Treatment for more than 60 days is preferred and treatment for at least 6 months is particularly preferred. The precise duration of treatment will depend on the patient's condition and response to treatment.

Patients treatable according to the invention will typically score low on the rating scales designed to or containing subscales to measure agitation.

Combination Therapy

The methods of the invention also contemplate administering ROCK inhibitors such as fasudil with other compounds used to treat dementia or other symptoms of dementia. They may be administered in combination, a single dosage form, in a common dosing regimen or administered to the same patient at different times of the day using different dosing regiments.

In some embodiments, the patients are administered fasudil in combination with other actives approved to treat to cholinesterase inhibitors and NMDA receptor antagonists. In one embodiment, the cholinesterase inhibitor is selected from the group consisting of donepezil, rivastigmine, and galantamine. Exemplary doses of the cholinesterase inhibitors include 3-25 mg per day, more preferably 6-12 mg per day. In another embodiment, the NMDA receptor antagonist is memantine. In a specific embodiment, memantine is administered at a dose of 5-28 mg per day, preferably 15-20 mg per day. In a further embodiment, the co-administered active is a combination of donepezil and memantine at a dose of 28 mg memantine and 10 mg donepezil.

In a specific embodiment, the combination of fasudil with cholinesterase inhibitors is administered to agitated patients with proteinopathy-associated cortical dementia. In a further embodiment, the combination of fasudil with cholinesterase inhibitors is administered to agitated patients with mixed dementia.

In yet a further embodiment, the combination of fasudil with cholinesterase inhibitors is not administered to agitated patients with only vascular cortical dementia.

Dextromethorphan hydrobromide is another an uncompetitive NMDA receptor antagonist that also has activity as a sigma-1 receptor agonist. Marketed in combination quinidine sulfate (a CYP450 2D6 inhibitor), the product Nudexta is indicated for the treatment of pseudobulbar affect, which occurs in many forms of dementia.

In an embodiment, the treatment with fasudil reduces or eliminates the need for use of mood stabilizers, benzodiazepines, antipsychotics, anti-agitation drugs, or sleep aids.

In a further embodiment, the patient treated with fasudil is not also being treated with active agents including mood stabilizers, benzodiazepines, antipsychotics, anti-agitation drugs, or sleep aids. In a specific embodiment, the patient treated with fasudil is not being treated with haloperidol, risperidone, aripiprazole, quetiapine, olanzapine, ziprasidone, lumateperone, carbamazepine, gabapentin, or valproate.

In another embodiment, the patient is being treated with the foregoing active agents but still exhibits agitation warranting treatment with fasudil. In one embodiment, fasudil treatment enables the patient to halt treatment with one of the drugs.

In another specific embodiment, the patient treated with fasudil is not being treated with an anti-anxiety medication. Anti-anxiety medications, which include alprazolam (Xanax), buspirone (BuSpar), lorazepam (Ativan), and oxazepam (Serax), often cause drowsiness. Paradoxically, they may also worsen confusion and agitation.

In a further embodiment the patient treated with fasudil can be treated for depression. In a specific embodiment, the patient is co-treated with fasudil and an anti-depressant such as citalopram or escitalopram or trazodone or other selective serotonin-reuptake inhibitors. In a preferred embodiment, the co-therapeutic is citalopram at 20-40 mg/day.

In an embodiment, the patient treated with fasudil is not being treated with an anti-depressant.

In one embodiment, fasudil can be co-administered with dextromethorphan with quinidine. In another embodiment, fasudil can be co-administered with prazosin.

Pharmaceutical Compositions

Oral dosage forms. Pharmaceutical compositions of ROCK inhibitors for oral administration may be in the form of tablets or capsules and may be immediate-release formulations or may be controlled- or extended-release formulations, which may contain pharmaceutically acceptable excipients, such as corn starch, mannitol, povidone, magnesium stearate, talc, cellulose, methylcellulose, carboxymethylcellulose and similar substances. A pharmaceutical composition comprising a ROCK inhibitor and/or a salt thereof may comprise one or more pharmaceutically acceptable excipients, which are known in the art. Formulations include oral films, orally disintegrating tablets, effervescent tablets and granules or beads that can be sprinkled on food or mixed with liquid as a slurry or poured directly into the mouth to be washed down.

Pharmaceutical compositions containing ROCK inhibitors, salts and hydrates thereof can be prepared by any method known in the art of pharmaceutics. In general, such preparatory methods include the steps of bringing a ROCK inhibitor or a pharmaceutically acceptable salt thereof into association with a carrier or excipient, and/or one or more other accessory ingredients, and then, if necessary and/or desirable, shaping, and/or packaging the product into a desired single- or multi-dose unit.

Pharmaceutical compositions can be prepared, packaged, and/or sold in bulk, as a single unit dose, and/or as a plurality of single unit doses. As used herein, a "unit dose" is a discrete amount of the pharmaceutical composition comprising a predetermined amount of the active ingredient. The amount of the active ingredient is generally equal to the dosage of the active ingredient which would be administered to a subject and/or a convenient fraction of such a dosage such as, for example, one-half or one-third of such a dosage.

Relative amounts of the active ingredient, the pharmaceutically acceptable excipient, and/or any additional ingredients in a pharmaceutical composition of the invention will vary, depending upon the identity, size, and/or condition of the subject treated and further depending upon the route by which the composition is to be administered. The composition used in accordance with the methods of the present invention may comprise between 0.001% and 100% (w/w) active ingredient.

Pharmaceutically acceptable excipients used in the manufacture of provided pharmaceutical compositions include inert diluents, dispersing and/or granulating agents, surface active agents and/or emulsifiers, disintegrating agents, binding agents, preservatives, buffering agents, lubricating agents, and/or oils. Excipients such as cocoa butter and suppository waxes, coloring agents, coating agents, sweetening, flavoring, and perfuming agents may also be present in the composition.

In certain embodiments, the pharmaceutical composition used in the methods of the present invention may comprise a diluent. Exemplary diluents include calcium carbonate, sodium carbonate, calcium phosphate, dicalcium phosphate, calcium sulfate, calcium hydrogen phosphate, sodium phosphate lactose, sucrose, cellulose, microcrystalline cellulose, kaolin, mannitol, sorbitol, inositol, sodium chloride, dry starch, cornstarch, powdered sugar, and mixtures thereof.

In certain embodiments, the pharmaceutical composition used in the methods of the present invention may comprise a granulating and/or dispersing agent. Exemplary granulating and/or dispersing agents include potato starch, corn starch, tapioca starch, sodium starch glycolate, clays, alginic acid, guar gum, citrus pulp, agar, bentonite, cellulose, and wood products, natural sponge, cation-exchange resins, calcium carbonate, silicates, sodium carbonate, cross-linked poly(vinyl-pyrrolidone) (crospovidone), sodium carboxymethyl starch (sodium starch glycolate), carboxymethyl cellulose, cross-linked sodium carboxymethyl cellulose (croscarmellose), methylcellulose, pregelatinized starch (starch 1500), microcrystalline starch, water insoluble starch, calcium carboxymethyl cellulose, magnesium aluminum silicate (VEEGUM), sodium lauryl sulfate, quaternary ammonium compounds, and mixtures thereof.

In certain embodiments, the pharmaceutical composition used in the methods of the present invention may comprise a binding agent. Exemplary binding agents include starch (e.g., cornstarch and starch paste), gelatin, sugars (e.g., sucrose, glucose, dextrose, dextrin, molasses, lactose, lactitol, mannitol, etc.), natural and synthetic gums (e.g., acacia, sodium alginate, extract of Irish moss, panwar gum, ghatti gum, mucilage of isapol husks, carboxymethylcellulose, methylcellulose, ethylcellulose, hydroxyethylcellulose, hydroxypropyl cellulose, hydroxypropyl methylcellulose, microcrystalline cellulose, cellulose acetate, poly(vinyl-pyrrolidone), magnesium aluminum silicate (VEEGUM®), and larch arabogalactan), alginates, polyethylene oxide, polyethylene glycol, inorganic calcium salts, silicic acid, polymethacrylates, waxes, water, alcohol, and/or mixtures thereof.

In certain embodiments, the pharmaceutical composition used in the methods of the present invention may comprise a preservative. Exemplary preservatives include antioxidants, chelating agents, antimicrobial preservatives, antifungal preservatives, antiprotozoan preservatives, alcohol preservatives, acidic preservatives, and other preservatives. In certain embodiments, the preservative is an antioxidant. In other embodiments, the preservative is a chelating agent.

In certain embodiments, the pharmaceutical composition used in the methods of the present invention may comprise an antioxidant. Exemplary antioxidants include alpha tocopherol, ascorbic acid, ascorbyl palmitate, butylated hydroxyanisole, butylated hydroxytoluene, monothioglycerol, potassium metabisulfite, propionic acid, propyl gallate, sodium ascorbate, sodium bisulfate, sodium metabisulfite, and sodium sulfite.

In certain embodiments, the pharmaceutical composition used in the methods of the present invention may comprise a chelating agent. Exemplary chelating agents include ethylenediaminetetraacetic acid (EDTA) and salts and hydrates thereof (e.g., sodium edetate, disodium edetate, trisodium edetate, calcium disodium edetate, dipotassium edetate, and the like), citric acid and salts and hydrates thereof (e.g., citric acid monohydrate), fumaric acid and salts and hydrates thereof, malic acid and salts and hydrates thereof, phosphoric acid and salts and hydrates thereof, and tartaric acid and salts and hydrates thereof. Exemplary antimicrobial preservatives include benzalkonium chloride, benzethonium chloride, benzyl alcohol, bronopol, cetrimide, cetylpyridinium chloride, chlorhexidine, chlorobutanol, chlorocresol, chloroxylenol, cresol, ethyl alcohol, glycerin, hexetidine, imidurea, phenol, phenoxyethanol, phenylethyl alcohol, phenylmercuric nitrate, propylene glycol, and thimerosal.

In certain embodiments, the pharmaceutical composition may comprise a buffering agent together with the ROCK inhibitor or the salt thereof. Exemplary buffering agents include citrate buffer solutions, acetate buffer solutions, phosphate buffer solutions, ammonium chloride, calcium carbonate, calcium chloride, calcium citrate, calcium glubionate, calcium gluceptate, calcium gluconate, D-gluconic acid, calcium glycerophosphate, calcium lactate, propanoic acid, calcium levulinate, pentanoic acid, dibasic calcium phosphate, phosphoric acid, tribasic calcium phosphate, calcium hydroxide phosphate, potassium acetate, potassium chloride, potassium gluconate, potassium mixtures, dibasic potassium phosphate, monobasic potassium phosphate, potassium phosphate mixtures, sodium acetate, sodium bicarbonate, sodium chloride, sodium citrate, sodium lactate, dibasic sodium phosphate, monobasic sodium phosphate, sodium phosphate mixtures, tromethamine, magnesium hydroxide, aluminum hydroxide, alginic acid, pyrogen-free water, isotonic saline, Ringer's solution, ethyl alcohol, and mixtures thereof.

In certain embodiments, the pharmaceutical composition used in the methods of the present invention may comprise a lubricating agent. Exemplary lubricating agents include magnesium stearate, calcium stearate, stearic acid, silica, talc, malt, glyceryl behanate, hydrogenated vegetable oils, polyethylene glycol, sodium benzoate, sodium acetate, sodium chloride, leucine, magnesium lauryl sulfate, sodium lauryl sulfate, and mixtures thereof.

In other embodiments, the pharmaceutical composition of containing a ROCK inhibitor or salt thereof will be administered as a liquid dosage form. Liquid dosage forms for oral and parenteral administration include pharmaceutically acceptable emulsions, microemulsions, solutions, suspensions, syrups, and elixirs. In addition to the active ingredients, the liquid dosage forms may comprise inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (e.g., cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can include adjuvants such as wetting agents, emulsifying and suspending agents, sweetening, flavoring, and perfuming agents.

Solid dosage forms for oral administration include capsules, tablets, pills, powders, and granules. In such solid dosage forms, the active ingredient is mixed with at least one inert, pharmaceutically acceptable excipient or carrier such as sodium citrate or dicalcium phosphate and/or (a) fillers or extenders such as starches, lactose, sucrose, glucose, mannitol, and silicic acid, (b) binders such as, for example, carboxymethylcellulose, alginates, gelatin, polyvinylpyrrolidinone, sucrose, and acacia, (c) humectants such as glycerol, (d) disintegrating agents such as agar, calcium carbonate, potato or tapioca starch, alginic acid, certain silicates, and sodium carbonate, (e) solution retarding agents such as paraffin, (f) absorption accelerators such as quaternary ammonium compounds, (g) wetting agents such as, for example, cetyl alcohol and glycerol monostearate, (h) absorbents such as kaolin and bentonite clay, and (i) lubricants such as talc, calcium stearate, magnesium stearate, solid polyethylene glycols, sodium lauryl sulfate, and mixtures thereof. In the case of capsules, tablets, and pills, the dosage form may include a buffering agent.

Some compositions of the invention relate to extended- or controlled-release formulations. These may be, for example, diffusion-controlled products, dissolution-controlled products, erosion products, osmotic pump systems or ionic resin systems. Diffusion-controlled products comprise a water-insoluble polymer which controls the flow of water and the subsequent egress of dissolved drug from the dosage from. Dissolution-controlled products control the rate of dissolution of the drug by using a polymer that slowly solubilizes or by microencapsulation of the drug-using varying thicknesses to control release. Erosion products control release of drug by the erosion rate of a carrier matrix. Osmotic pump systems release a drug based on the constant inflow of water across a semi permeable membrane into a reservoir which contains an osmotic agent. Ion exchange resins can be used to bind drugs such that, when ingested, the release of drug is determined by the ionic environment within the gastrointestinal tract.

Parenteral dosage forms. Fasudil can be administered in parenteral dosage forms. The term "parenteral," as used herein, includes, but is not limited to, subcutaneous injections, intravenous, intramuscular, intraperitoneal injections, or infusion techniques.

Pharmaceutical compositions or formulations suitable for parenteral administration include aqueous and non-aqueous sterile injection solutions which may contain antioxidants, buffers, bacteriostats and solutes that render the formulation isotonic with the blood of the intended recipient; and aqueous and non-aqueous sterile suspensions which may include suspending agents and thickening agents. The compositions may be presented in unit-dose or multi-dose containers, sealed ampules and vials, and may be stored in a freeze-dried (lyophilized) condition requiring only the addition of the sterile liquid carrier, water for injections, immediately prior to use. Extemporaneous injection solutions and suspensions may be prepared from sterile powders, granules and tablets of the kind previously described.

Parenteral pharmaceutical formulation may further contain other acceptable liquid carriers in an amount that does not alter the aqueous nature of the formulation, including, vegetable oils such as peanut oil, cotton seed oil, sesame oil, as well as organic solvents, PEG, propylene glycol, glycerol, and surfactants. In certain embodiments for parenteral administration, the conjugates of the invention are mixed with solubilizing agents such as Cremophor™, alcohols, oils, modified oils, glycols, polysorbates, cyclodextrins, polymers, and mixtures thereof.

Parenteral formulations may further comprise at least one of any suitable auxiliaries including, but not limited to, diluents, crystal inhibitors, tonicifiers, water structure forming agents or disruptors, polymers, ion pairing agents, stabilizers, buffers, salts, lipophilic solvents, preservatives, adjuvants or the like. Pharmaceutically acceptable auxiliaries are preferred. Examples and methods of preparing such sterile solutions are well known in the art and can be found in well-known texts such as, but not limited to, REMINGTON'S PHARMACEUTICAL SCIENCES (Gennaro, Ed., 18th Edition, Mack Publishing Co. (1990); Handbook of Pharmaceutical Excipients, $9^{th}$ Edition, Pharmaceutical Press (2020)). Pharmaceutically acceptable carriers can be routinely selected that are suitable for the mode of administration, solubility and/or stability of the compound.

In one embodiment, the aqueous parenteral pharmaceutical formulation comprises at least 50% water, preferably 70% or more of water. The pharmaceutical compositions may be prepared by dissolving or suspending the compound in the liquid carrier such that the final formulation contains from about 0.005% to 30% by weight of a compound.

Routes of administration and dosages of effective amounts of the aqueous parenteral pharmaceutical formulations comprising fasudil are also provided. For parenteral administration, sterile suspensions and solutions are desired. Isotonic preparations which generally contain suitable preservatives are employed when intravenous, administration is desired. The pharmaceutical compositions may be administered parenterally via injection of a pharmaceutical composition comprising fasudil dissolved in an inert liquid carrier.

The preferred route of parenteral administration is intravenous. The pharmaceutical formulations described herein may also be administered by infusion. The pharmaceutical formulations described herein may also be administered by a bolus dosage, optionally combined with administration by infusion. The compounds described herein can be administered in combination with other pharmaceutical agents in a variety of protocols for effective treatment of disease.

Example 1

A clinical trial was conducted to determine the effectiveness of oral fasudil in reducing the agitation in patients with Alzheimer's Dementia (AD).

Nineteen patients with Alzheimer's Dementia were recruited and treated for 6-12 weeks with fasudil HCl hemihydrate. All the patients were treated for 6 weeks with 90 mg per day (30 mg TID) and a subset of patients was treated an additional 6 weeks with 180 mg per day (60 mg TID). Both treatment regimens were well tolerated. A variety of assessments were conducted at baseline and at the end of treatment, including the NPI-Q and the CMAI.

At the end of treatment, patients were selected on the basis of a minimum threshold of agitation at baseline (not all patients had agitation of a specific threshold at baseline and to demonstrate an agitation treatment effect, the threshold provided a population with a greater deficit from which to show improvement). Two baseline thresholds were set, and two analyses were done based on the two groupings that resulted. One threshold was based on the agitation/aggression domain of the NPI-Q and the other based on the CMAI score. The NPI-Q-based selection threshold resulted in a smaller group of patients than the CMAI-based threshold, but when each group was analyzed using the CMAI score (the gold-standard agitation assessment, required by the FDA), the results were very similar.

The first selection was based on NPI-Q score of ≥4. This threshold yielded six patients who had a mean CMAI score of 45.3 at baseline. All members of this subgroup were treated with 90 mg per day (30 mg TID) of fasudil for 6 weeks.

Results: The six patients with an NPI-Q score of ≥4 had a mean CMAI score of 45.3 at baseline and a mean of 23.0 at the end of treatment for a difference of 22.3. This is shown in FIG. 1.

The second selection required a baseline CMAI score of ≥20 and this yielded a 13-patient subgroup, having a mean baseline CMAI score of 34.4. All patients in the second subgroup were treated for 6 weeks at 90 mg per day (30 mg TID) of fasudil and three of the thirteen were treated for an additional 6 weeks with 180 mg per day (60 mg TID) of fasudil. All the patients selected using the NPI-Q agitation/aggression domain score of ≥4 were also included in this subgroup.

The analysis looked at the CMAI score prior to treatment and compared it to the last day of treatment (6 weeks for the 10 patients on the low dose and 12 weeks for the 3 patients on the high dose).

Figure 2:
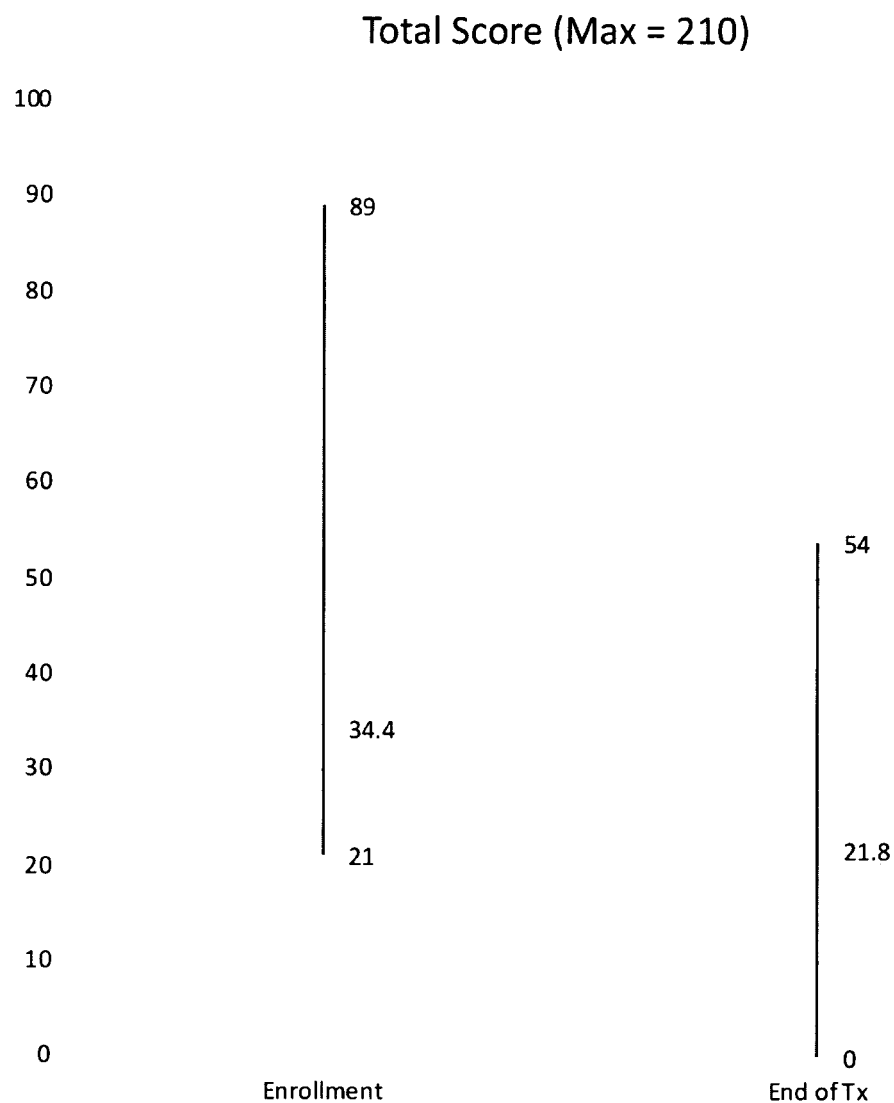
FIG. 2 shows the change from baseline in the CMAI in thirteen patients treated with fasudil who had a mean baseline CMAI score of 34.4.

Results: The thirteen patients with a CMAI score of ≥20 had a mean CMAI score of 34.4 prior to treatment and 21.8 at the end of treatment for a difference of 12.6. This is shown in FIG. 2.

The results in both groups of patients are highly relevant. A change of less than 5 points on the CMAI is considered clinically meaningful and these changes are several-fold greater. The NPI-Q threshold resulted in a more stringent selection and a more dramatic effect, but the CMAI threshold also resulted in a meaningful change and so either threshold can be considered in patient selection for treatment.

Figure 3:
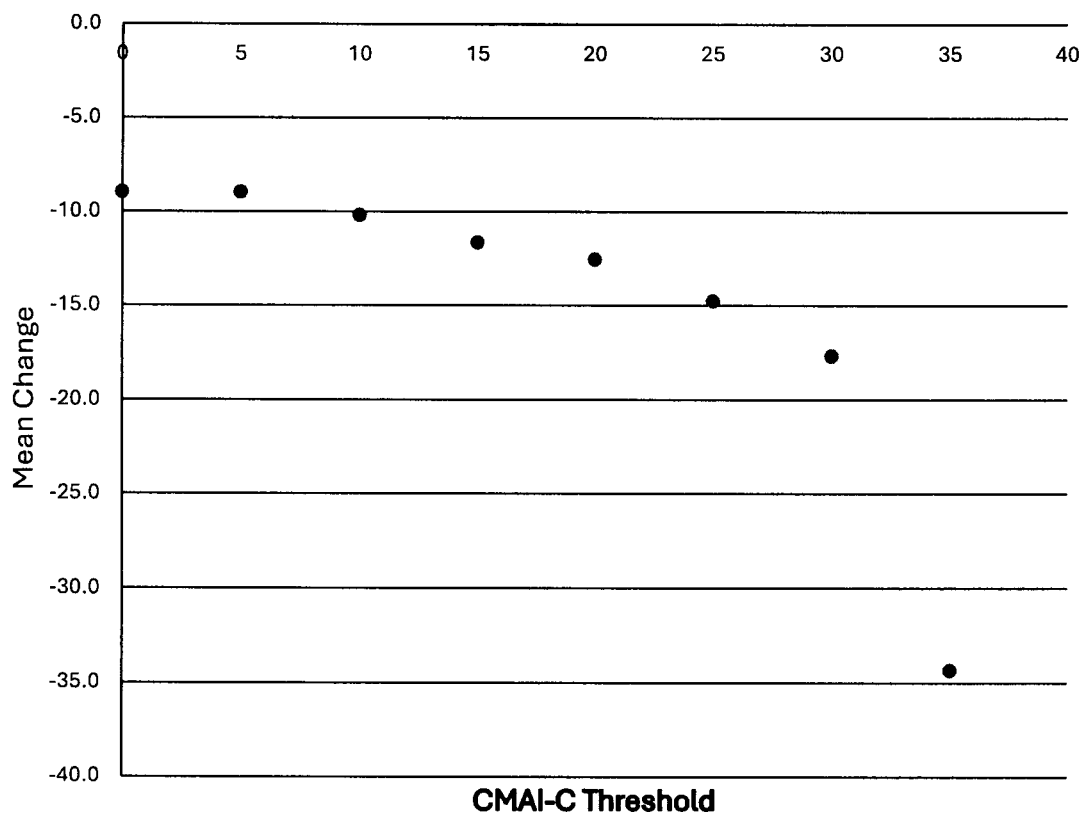
FIG. 3 shows the effects of changing the CMAI-C threshold in 5-point increments in patients treated with fasudil.

Finally, to examine the effects of changing the CMAI-C threshold, 5-point increments were used to move the cutoff from 0 to 35. As the threshold increased, so did the magnitude of the observed effect. It was concluded that setting the CMAI-C threshold of at least 5 provided a meaningful result over the population, even though higher thresholds we more powerful at detecting change. This is shown in FIG. 3.

LIST OF REFERENCES

Charernboon T, Phanasathit M, Prevalence of neuropsychiatric symptoms in Alzheimer's disease: a cross-sectional descriptive study in Thailand. J Med Assoc Thai. 2014; 97, 560-565.

Chen M, Liu A, Ouyang Y, Huang Y, Chao X, Pi R. 2013. Fasudil and its analogs: a new powerful weapon in the long war against central nervous system disorders? Expert Opin Investig Drugs. 22:537-50.

Cohen-Mansfield, Agitated behaviours in the elderly: II. Preliminary results in the cognitively deteriorated. JAGS. 1986; 34:722-7

Cummings J L. The Neuropsychiatric Inventory: assessing psychopathology in dementia patients. Neurology. 1997; 48(Suppl 6):S10-6.

Dennehy E B et al., Derivation of a brief measure of agitation and aggression in Alzheimer's disease. Int. Geriatr Psychiatry. 2013; 28(2): 182-9.

de Medeiros K et al., The Neuropsychiatric Inventory-Clinician rating scale (NPI-C): reliability and validity of a revised assessment of neuropsychiatric symptoms in dementia. Int. Psychogeriatr. 2010; 22(6): 984-94.

Feng Y, LoGrasso P, Defert O, Li R, Rho Kinase (ROCK) Inhibitors and Their Therapeutic Potential. J Med Chem. 2016; 59*6): 2269-2300.

Greathouse et al., Fasudil or genetic depletion of ROCK1 or ROCK2 induces anxiety-like behaviors. Behavioural Brain Research. 2019; 373:112083.

Jacobs M, Hayakawa K, Swenson L, Bellon S, Fleming M, Taslimi P, Doran J, The structure of dimeric ROCK I reveals the mechanism for ligand selectivity. J Biol Chem. 2006; 281(1): 260-68.

Kaufer et al, Assessing the impact of neuropsychiatric symptoms in Alzheimer's disease: The neuropsychiatric inventory caregiver distress scale. JAGS, 1998; 46:210-215.

Maust D T et al., Antipsychotics, other psychotropics, and the risk of death in patients with dementia: number needed to harm. JAMA Psychiatry. 2015; 72(5): 438-45.

Monteiro I M et al., Addition of a frequency-weighted score to the Behavioral Pathology in Alzheimer's Disease Rating Scale: the BEHAVE-AD-FW: methodology and reliability. Eur Psychiatry. 2001 January; 16 Suppl 1:5s-24s.

Nakagawa O, Fukisawa K, Ishizaki T, Saito Y, Nakao K, Narumiya S, ROCK-I and ROCK-II, two isoforms of Rho-associated coiled-coil forming protein serine/threonine kinase in mice. FEBS Lett. 1996 Aug. 26; 392(2): 189-93.

Ryu et al., Persistence of and changes in neuropsychiatric symptoms in Alzheimer disease over 6 months: the LASER-AD study. Am. J. Geriatr. Psychiatry. 2005; 13(11):976-83.

Shibuya M, Asano T, Sasaki Y. 2001. Effect of Fasudil HCl, a protein kinase inhibitor, on cerebral vasospasm. Acta Neurochir Suppl. 77:201-4.

Schneider L S, Olin J T, Doody R S, Clark C M, Morris J C, Reisberg B, et al. The Alzheimer's Disease Cooperative Study. Validity and reliability of the Alzheimer's Disease Cooperative Study—Clinical Global Impression of Change. Alzheimer Dis Assoc Disord. 1997; 11(Suppl 2):S22-32.

Trachtenberg et al., Comorbidity of Psychopathological Domains in Community-Dwelling Persons With Alzheimer's Disease. J. Geriatr. Psychiatry. Neurol. 2003; 16(2): 94-99.

Uehata M, Ishizaki T, Satoh H, Ono T, Kawahara T, Morishita T, Tamakawa H, Yamagami K, inui J, Maekawa M, Narumiya S, Calcium sensitization of smooth muscle mediated by a Rho-associated protein kinase in hypertension. Nature. 1997 Oct. 30; 389(6654):990-4.

Yamaguchi H, Miwa Y, Kasa M, Kitano K, Amano M, Kaibuchi K, Hakoshima T, Structural basis for induced-fit binding of Rho-kinase to the inhibitor Y-27632. J Biochem. 2006 September; 140(3):305-11.

The disclosure of each reference set forth herein is incorporated herein by reference in its entirety.

The invention claimed is:

1. A method of treating agitation in an Alzheimer's disease dementia patient, comprising orally administering to the patient a therapeutically effective amount of fasudil at a dose of 90 mg to 240 mg per day in an immediate release formulation, wherein the patient before treatment has a minimum score on the Cohen-Mansfield Agitation Index (CMAI) of $\geq 20$, and wherein the patient treated with fasudil exhibits an improvement on the CMAI of at least 5 points from the patient's score before treatment with fasudil.

2. The method according to claim 1, wherein the agitation comprises aggression, hostility, delusions, hallucinations, suspiciousness, insomnia, or aberrant motor behaviors.

3. The method according to claim 1, wherein the fasudil is fasudil hydrochloride hemihydrate.

4. The method according to claim 3, wherein the patient is administered a total daily dose of 90 mg fasudil hydrochloride hemihydrate at 30 mg TID.

5. The method according to claim 1, where the patient is displaying at least one type of agitation as measured by the CMAI-C selected from the group consisting of physically aggressive, verbally aggressive, physically non-aggressive, and verbally non-aggressive.

6. The method according to claim 1, wherein the patient treated with fasudil exhibits an improvement on the CMAI-C of at least about 12 points from the patient's baseline score before treatment with fasudil.

7. A method of treating agitation in an Alzheimer's disease dementia patient, comprising orally administering to the patient a therapeutically effective amount of fasudil at a dose of 90 mg to 240 mg per day in an immediate release formulation, wherein the patient before treatment has a minimum Neuropsychiatric Inventory-Questionnaire (NPI-Q) agitation/aggression domain score of $\leq 4$.

8. The method according to claim 7, wherein the patient treated with fasudil exhibits an improvement on the NPI-Q agitation/aggression domain of at least about 1 point to at least about 3 points from the patient's baseline score before treatment with fasudil.

9. The method according to claim 1, wherein the fasudil treatment reduces the number of occurrences of agitation over a time period.

10. The method according to claim 9, wherein the fasudil treatment reduces occurrences of agitation per day.

11. The method according to claim 9, wherein the fasudil treatment reduces the number of days per week agitation occurs.

12. The method according to claim 9, wherein the fasudil treatment reduces the number of occurrences of agitation per week.

13. The method according to claim 1, wherein the fasudil treatment delays the increase in agitation that occurs in dementia patients as the severity of dementia progresses.

14. The method according to claim 1, wherein the patient does not exhibit wandering behavior consisting of elopement, boundary transgressions, or wayfinding defects.

15. The method according to claim 1, wherein the patient does not exhibit pacing, looping, or excessive walking.

16. The method according to claim 1, wherein the patient has not previously been treated with fasudil for chronic stroke.

17. The method according to claim 7, wherein the patient before treatment has a minimum Neuropsychiatric Inventory-Questionnaire (NPI-Q) agitation/aggression domain score of $\geq 6$.

18. The method according to claim 7, wherein the fasudil treatment reduces the lumber of occurrences of agitation over a time period.

19. The method according to claim 18, wherein the fasudil treatment reduces occurrences of agitation per day.

20. The method according to claim 18, wherein the fasudil treatment reduces the number of days per week agitation occurs.

21. The method according to claim 18, wherein the fasudil treatment reduces the number of occurrences of agitation per week.

22. The method according to claim 7, wherein the fasudil treatment delays the increase in agitation that occurs in dementia patients as the severity of dementia progresses.

23. The method according to claim 7, wherein the patient does not exhibit wandering behavior consisting of elopement, boundary transgressions, or wayfinding defects.

24. The method according to claim 7, wherein the patient does not exhibit pacing, looping, or excessive walking.

25. The method according to claim 7, wherein the patient has not previously been treated with fasudil for chronic stroke.

26. The method according to claim 1, wherein the fasudil treatment reduces the length of time, or the severity, of early evening agitation.

27. The method according to claim 7, wherein the fasudil treatment reduces the length of time, or the severity, of early evening agitation.

\* \* \* \* \*